United States Patent
Myrman (10) Patent No.: US 10,376,225 B2
(45) Date of Patent: Aug. 13, 2019

(54) SCANNING X-RAY IMAGING DEVICE WITH VARIABLE SHIELD PLATES AND METHOD FOR OPERATING SAME

(71) Applicant: KONINKLIJKE PHILIPS N.V., Eindhoven (NL)

(72) Inventor: Per Mattias Myrman, Tyresö (SE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 351 days.

(21) Appl. No.: 15/101,957

(22) PCT Filed: Dec. 4, 2014

(86) PCT No.: PCT/EP2014/076474
§ 371 (c)(1),
(2) Date: Jun. 6, 2016

(87) PCT Pub. No.: WO2015/086412
PCT Pub. Date: Jun. 18, 2015

(65) Prior Publication Data
US 2016/0310087 A1 Oct. 27, 2016

(30) Foreign Application Priority Data

Dec. 9, 2013 (EP) ..................................... 13196323

(51) Int. Cl.
*A61B 6/03* (2006.01)
*A61B 6/06* (2006.01)
(Continued)

(52) U.S. Cl.
CPC ................ *A61B 6/06* (2013.01); *A61B 6/405* (2013.01); *A61B 6/4035* (2013.01);
(Continued)

(58) Field of Classification Search
CPC combination set(s) only.
See application file for complete search history.

(56) References Cited

U.S. PATENT DOCUMENTS 4,143,273 A * 3/1979 Richey .................. A61B 6/032
378/150
4,953,192 A 8/1990 Plewes
(Continued)

FOREIGN PATENT DOCUMENTS

WO 2007/050025 5/2007
WO 2009/083850 7/2009

*Primary Examiner* — Don K Wong
(74) *Attorney, Agent, or Firm* — Larry Liberchuk (57) ABSTRACT

A scanning X-ray imaging device (100) is proposed. The device may be specifically adapted for mammography applications. The device comprises an X-ray source (110), an X-ray line detector (150), a field limiter arrangement (170) and an observation volume (135). The field limiter arrangement (170) comprises at least two variable shield plates (174, 175) enclosing an opening (176) and a displacing mechanism (177). The shield plates may be displaced with respect to a center axis of an X-ray beam (115) by means of the displacing mechanism such as to vary at least one of a cross-section and a location of the opening (176) between the field plates (174, 175) through which at least a part of the X-ray beam (115) is transmitted. The shield plates may be displaced independently from each other by means of the displacing mechanism (177). Such device (100) may be operated to perform a scanning motion such as to scan at least portions of the X-ray beam through a region of interest within the observation volume (135) and, at the same time, control the displacing mechanism (177) such that the opening (176) between the field plates (174, 175) is first successively opened to a larger cross-section and then successively closed again to a smaller cross-section during the scanning motion. Thereby, an X-ray dose level and an X-ray exposure (Continued)

time may be kept constant throughout an image acquisition procedure and an overall dose level may be minimized.

12 Claims, 8 Drawing Sheets

(51) Int. Cl.
*A61B 6/00* (2006.01)
*G21K 1/04* (2006.01)

(52) U.S. Cl.
CPC ............ *A61B 6/4266* (2013.01); *A61B 6/502* (2013.01); *G21K 1/043* (2013.01)

(56) References Cited

U.S. PATENT DOCUMENTS

| | | |
|---|---|---|
| 8,031,834 B2 | 10/2011 | Ludwig |
| 2005/0053188 A1 | 3/2005 | Gohno |
| 2007/0025497 A1 | 2/2007 | Fujita |
| 2008/0317212 A1 | 12/2008 | Kuehn |
| 2010/0054395 A1 | 3/2010 | Noshi |
| 2010/0254508 A1 | 10/2010 | Von Der Haar |
| 2011/0013742 A1 | 1/2011 | Zaiki |
| 2012/0128120 A1* | 5/2012 | De Man ................ A61B 6/032 378/16 |

\* cited by examiner

SCANNING X-RAY IMAGING DEVICE WITH VARIABLE SHIELD PLATES AND METHOD FOR OPERATING SAME

CROSS REFERENCE TO RELATED APPLICATIONS

This application is the U.S. National Phase application under 35 U.S.C. § 371 of International Application No. PCT/EP2014/076474, filed Dec. 4, 2014, published as WO 2015/086412 on Jun. 18, 2015, which claims the benefit of European Patent Application Number 13196323.3 filed Dec. 9, 2013. These applications are hereby incorporated by reference herein.

FIELD OF THE INVENTION

The present invention relates to a scanning X-ray imaging device and to a method for operating such device. Furthermore, the invention relates to a computer program product comprising computer-readable code for performing the inventive method as well as a computer-readable medium comprising such computer program product stored thereon.

BACKGROUND OF THE INVENTION

X-ray imaging is applied in various technical fields in order to obtain information about internal structures within a region of interest of an object. For example, medical X-ray imaging devices are used to obtain information about internal structures within a patient's body.

Basically, an X-ray imaging device comprises at least an X-ray source and an X-ray detector arranged at opposite sides of an observation volume in which the region of interest is to be placed.

In a stationary approach, both the X-ray source and the X-ray detector are arranged at fixed locations and X-rays coming from the X-ray source are transmitted through the region of interest in the observation volume and are partly attenuated therein and are then detected by the X-ray detector. In such approach, the X-ray detector is typically a two-dimensional X-ray detector having multiple detector elements arranged in a two-dimensional matrix. In such approach, a field of view is generally determined by the size of the two-dimensional X-ray detector.

In an alternative approach, at least one of the X-ray source and the X-ray detector is not stationary but is moved during an image acquisition procedure. In such approach, the X-ray detector is typically substantially smaller than the cross-section of the region of interest such that an image of the entire region of interest may not be acquired for all sub-regions of the region of interest simultaneously. Accordingly, in such dynamic approach, an entire image is acquired by successively scanning the X-ray beam and/or the X-ray detector along the region of interest. Image information is acquired for each of the sub-regions of the region of interest successively and the entire image may be derived by combining the image information of all sub-regions. For example, an X-ray line detector comprising multiple X-ray detector elements arranged as a one-dimensional matrix, i.e. arranged along a line, may be used for acquiring an entire image of a region of interest by scanning the line detector in a direction perpendicular to the line direction of the detector.

In a further improved embodiment of such scanning approach, the X-ray detector does not only comprise a single X-ray line detector but comprises a plurality of X-ray line detectors arranged one behind the other with respect to the scanning direction. In such approach, most of the sub-regions of the region of interest are not only scanned by a single X-ray line detector but during the image acquisition procedure, image information for this sub-region is acquired successively by a multiplicity of X-ray line detectors.

For example, WO 2007/050025 A2 discloses a method and arrangement relating to X-ray imaging in which an X-ray apparatus comprises an X-ray source for generating X-rays emerging from a focal spot, a multi-slit collimator, a line detector assembly and an exposure volume arranged between the collimator and the detector assembly. The line detector assembly comprises multiple lines of X-ray detector elements. The X-ray source, the collimator and the detector assembly are arranged in series so that each detector line is aligned with a corresponding collimator slit and simultaneously displaceable by a scan motion relative that exposure volume.

However, it has been observed that with conventional approaches of scanning X-ray imaging, there is a risk of excessive X-ray dose exposure at least when acquiring image information for some of the sub-regions within the region of interest. Such problem of X-ray overexposure may occur specifically in applications with only short scanning distances or angles. Furthermore, there may be a risk of motion blur due to patient movement during X-ray image acquisition.

SUMMARY OF THE INVENTION

Accordingly, there may be a need for a scanning X-ray imaging device and a method for operating such device enabling reducing X-ray dose exposure during image acquisition together with enabling acquiring high quality X-ray images. Furthermore, there may be a need for a computer program product instructing a computer for performing that method and for a computer-readable medium comprising such computer program product stored thereon.

Such needs may be met with the subject-matter of the independent claims. Further embodiments of the invention are defined in the dependent claims and in the subsequent specification.

According to a first aspect of the present invention, a scanning X-ray imaging device is proposed. The device comprises an X-ray source, an X-ray line detector, a field limiter arrangement and an observation volume. The X-ray source is adapted to emit an X-ray beam towards the X-ray line detector. A moving mechanism coupled to at least one of the X-ray source and the X-ray line detector, the moving mechanism adapted to perform a scanning motion such as to scan at least portions of the X-ray beam through a region of interest within the observation volume. The observation volume is arranged between the X-ray source and the X-ray line detector. The field limiter arrangement is arranged between the X-ray source and the observation volume. In addition, a collimator may preferably be arranged between the X-ray source and the observation volume to shape the X-ray field according to the X-ray sensitive elements of the X-ray sensitive line detector. The field limiter arrangement comprises at least two variable shield plates and a displacing mechanism. Therein, the shield plates may be displaced with respect to a center axis of the X-ray beam by means of the displacing mechanism such as to vary a cross-section and/or location of an opening between the shield plates through which at least a part of the X-ray beam is transmitted. Furthermore, the shield plates may be displaced independently from each other by means of the displacing mechanism. The independent displacing of the shield plates is controlled by the displacing mechanism such that the opening between the shield plates is first successively opened to a larger cross section and then successively closed again to a smaller cross section during the scanning motion.

According to an embodiment, the X-ray line detector comprises multiple lines of X-ray detector elements arranged in a line direction orthogonal to the X-ray beam. Therein, the displacement mechanism is adapted to displace each of the shield plates in a direction orthogonal to the line direction. In other words, the X-ray line detector may comprise multiple lines of detector elements each line being arranged orthogonal to a scanning direction and the lines of detector elements are arranged one behind the other along the scanning direction of the X-ray detector. Therein, the scanning direction of the X-ray detector is the direction along which the X-ray detector is moved during a scanning motion for acquiring an X-ray image of an entire region of interest. The shield plates shall be displaceable orthogonal to the lines of detector arrangements, i.e. for example substantially parallel or anti-parallel to the scanning direction.

Specifically, in such embodiment, the X-ray line detector may comprise more lines of X-ray detector elements than required for acquiring image information of sufficient image quality during a scanning motion. In other words, for example depending on a scanning velocity, it may be sufficient to acquire image information for each of the sub-regions in the region of interest using seven lines of X-ray detector elements wherein, during the scanning procedure, each of the lines of X-ray detector elements acquires image information of the respective sub-region successively and final image information for this sub-region may be obtained based on the information of all these seven lines of X-ray detector elements with a sufficient overall image quality. However, the X-ray line detector does not comprise only seven lines of X-ray detector elements but comprises significantly more lines such as for example 28 lines of X-ray detector elements.

According to an embodiment of the invention, the X-ray source and the X-ray line detector are coupled to a moving mechanism such that a center axis of the X-ray beam may be rotated around an axis orthogonal to the center axis. In other words, during a scanning motion, the X-ray source and the X-ray line detector may be moved by the moving mechanism such that none of both components is stationary but both components are moved in a synchronized manner such that the X-ray beam emitted by the X-ray source in a direction towards the X-ray detector and particularly the center axis of such X-ray beam is rotated, i.e. changes its orientation, during the scanning motion. For example, both the X-ray source and the X-ray line detector may be arranged on a common arm at two positions at opposite sides of an intermediate observation volume wherein the arm together with the X-ray source and the X-ray line detector may be pivoted in a scanning motion.

In such embodiment, the moving mechanism may be adapted to move the X-ray beam such as to displace the center axis of the X-ray beam within the observation volume in order to thereby scan the X-ray beam through the region of interest within the observation volume. In other words, in a scanning motion performed by the moving mechanism, the X-ray beam is not only rotated but its center axis is also displaced laterally within the observation volume such that the X-ray beam is transmitted through each of the various sub-regions of the region of interest during the scanning motion.

According to an embodiment, each of the shield plates is adapted to substantially absorb X-rays. For example, the shield plates may comprise a heavy material such as lead and may have a sufficient thickness in order to absorb at least 70%, preferably at least 90% of incident X-rays.

According to an embodiment of the invention, the X-ray imaging device is a scanning mammography X-ray imaging device. For example, the device may be adapted to support a female breast within the observation volume and to move the X-ray source and/or the X-ray detector relative to the female breast such as to scan a region of interest within the breast. Particularly, the mammography X-ray imaging device may be adapted for providing quasi-3D-imaging by acquiring at least two images from different viewing angles, sometimes referred to as stereo-imaging. Such quasi-3D-imaging may be particularly helpful for example in biopsy monitoring where a biopsy needle has to be observed while being introduced in a body part such as a female breast.

According to a second aspect of the present invention, a method for operating an X-ray imaging device as described above is proposed. The method comprises controlling the moving mechanism to perform a scanning motion such as to scan at least portions of the X-ray beam through a region of interest within the observation volume and controlling the displacing mechanism such that the opening between the shield plates is first successively opened to a larger cross-section and then successively closed again to a smaller cross-section during the scanning motion. In other words, during a scanning motion, the moving mechanism shall move the X-ray source and/or the X-ray line detector such that an X-ray beam is transmitted through all sub-regions of a region of interest successively, i.e. the X-ray beam is scanned. Simultaneously to such scanning motion, the shield plates of the field limiter arrangement shall be displaced using the displacing mechanism in a manner such that, first, an opening between the shield plates is successively enlarged from a minimum opening to a maximum opening cross-section and then, towards an end of the scanning motion, this opening is successively closed again to a minimum cross-section. As explained further below, such combination of scanning motion and displacing the shield plates of the field limiter arrangement may minimize an X-ray dose exposure during image acquisition and may additionally provide a more uniform image quality across the region of interest.

According to an embodiment, the displacement mechanism is controlled such that, during the scanning motion, a center of the opening between the shield plates of the field limiter arrangement moves irrelative to the X-ray line detector. In other words, during a scanning motion, the shield plates of the field limiter arrangement may be moved using the displacing mechanism in such a manner that the opening between the shield plates moves laterally in a plane substantially parallel to the X-ray line detector and thus moves relative to the X-ray line detector and, accordingly, a portion of the X-ray beam transmitted through this opening is moved along the surface of the X-ray line detector. Accordingly, during the scanning motion, a portion of the X-ray beam emitted by the X-ray source is not only scanned through the region of interest but also a partial area irradiated by this portion of the X-ray beam on the surface of the X-ray line detector moves along this surface during the scanning motion procedure.

According to an embodiment, at a beginning of an image acquisition procedure during the scanning motion, the displacing mechanism is controlled such that a minimum number of lines of X-ray detector elements closer to a first edge of the X-ray detector is irradiated through the opening between the shield plates and, at an end of the image acquisition procedure during the scanning motion, the displacing mechanism is controlled such that a minimum number of lines of X-ray detector elements closer to a second edge of the X-ray detector opposite to the first edge is irradiated through the opening between the shield plates. The first and the second edge in this case does not necessarily relate to the direction of the scan motion. In other words, in an image acquisition procedure, the displacing mechanism may be controlled at a beginning such that the opening between the shield plates of the field limiter arrangement has a minimum cross-section and thus a minimum number of lines of X-ray detector elements on the X-ray line detector are irradiated. During the image acquisition procedure, the displacing mechanism is then controlled to further open the opening between the shield plates before, towards the end of the image acquisition procedure, closing the opening again successively. However, in such opening and closing process, a center of the opening may not remain stationary but may move along the surface of the X-ray line detector such that at the beginning of the image acquisition procedure, X-ray detector elements closer to a first edge of the X-ray detector are irradiated whereas, at the end of the image acquisition procedure, X-ray detector elements closer to a second opposite edge of the X-ray detector are irradiated.

According to a further embodiment, a moving velocity with which the X-ray detector is moved during the scanning motion is smaller than a velocity with which the portion of the X-ray beam transmitted through the opening between the shield plates is displaced on a surface generated by the X-ray detector motion during the scanning motion. In other words, the shield plates of the field limiter arrangement may be displaced such that a displacement velocity of the opening between the shield plates in a lateral direction is high enough such that the portion of the X-ray beam transmitted through this opening is displaced laterally with such velocity such that, at a location of the surface of the X-ray detector, the X-ray beam moves faster than the motion of the X-ray detector itself. Accordingly, while both the X-ray detector and the X-ray beam portion transmitted through the opening of the field limiter arrangement move laterally during the scanning motion, the transmitted X-ray beam portion is moved at a higher velocity than the X-ray detector and is therefore also displaced relative to the X-ray detector.

According to a further embodiment, the X-ray imaging device is adapted to perform a method according to an embodiment as described above.

According to a third aspect, the present invention relates to a computer program product comprising computer-readable code which, when executed by a computer, instructs the computer to perform the method according to an embodiment as described above. The code may comprise computer-readable instructions in any computer programming language.

According to a fourth aspect of the present invention, a computer-readable medium comprising a computer program product as described above stored thereon is proposed. Therein, the computer-readable medium may be any medium on which computer-readable code may be stored such as e.g. a CD, a DVD, a flash memory, etc.

Briefly summarized, ideas underlying embodiments of the present invention may be understood as being based, inter alia, on the following thoughts and observations: In order to reduce X-ray dose and local object exposure time during X-ray imaging, particularly during scanning X-ray mammography, it is proposed to use a new type of variable field limiter where both shielding plates can move in an uncoupled manner. By controlling the movement of such shielding plates in a specific way, a portion of the region of interest being irradiated by part of the X-ray beam being transmitted through the variable field limiter may be adjusted such that an overall dose applied to the patient may be reduced and imaging quality may be substantially homogenous and/or improved.

It shall be noted that possible features and advantages of embodiments of the present invention are described herein partly with respect to a scanning X-ray imaging device and partly with respect to a method of operating such device. A person skilled in the art will realize that features of the imaging device and features of the method may be combined, replaced or adapted in suitable manners in order to come to further embodiments of the present invention.

BRIEF DESCRIPTION OF THE DRAWINGS

In the following, embodiments of the invention will be described with reference to the attached drawings wherein neither the description nor the drawings shall be interpreted as limiting the invention.

The figures are only schematical and not to scale. Same reference signs refer to same or similar features throughout the figures.

DETAILED DESCRIPTION OF EMBODIMENTS

Figure 1:
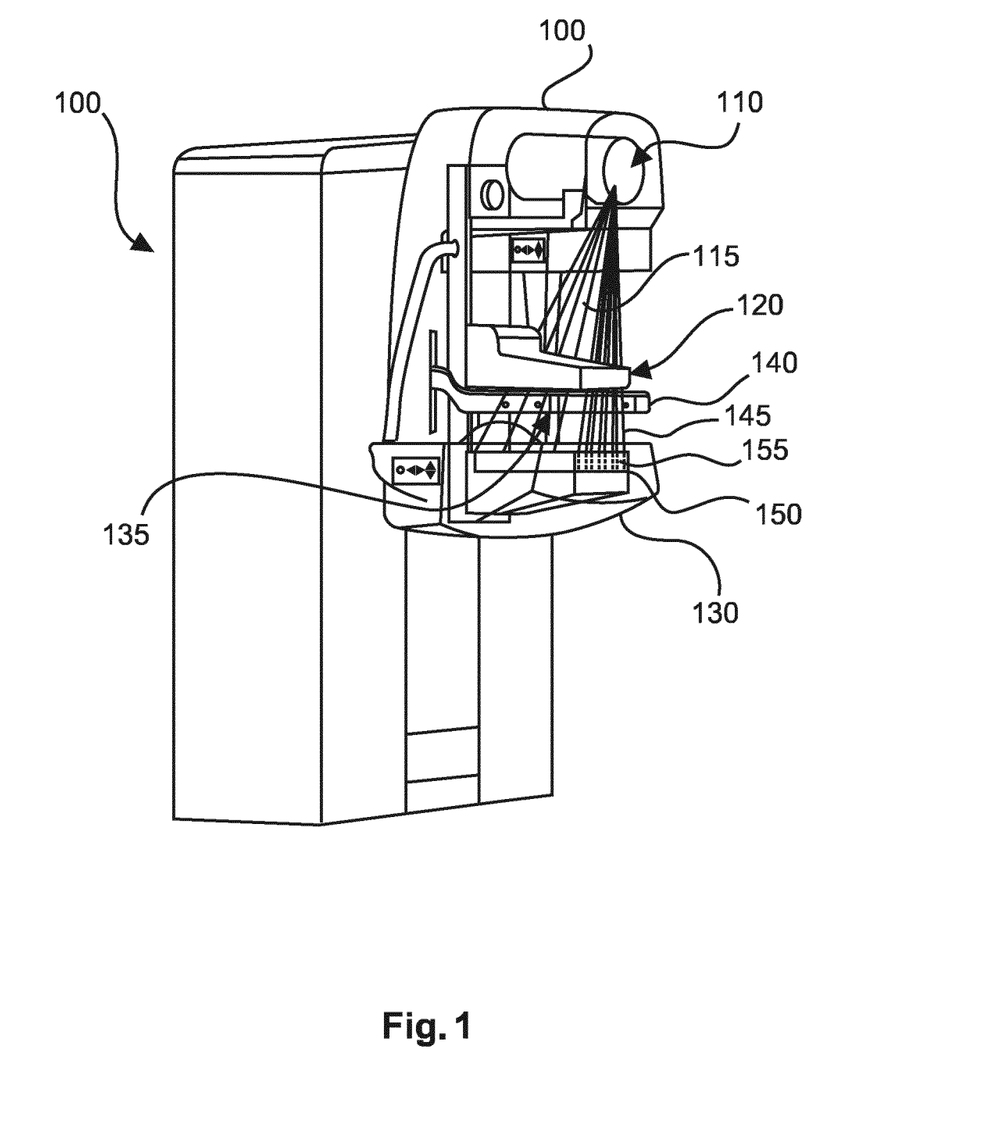
FIGS. 1 and 2 schematically illustrate a scanning mammography X-ray imaging device in which an embodiment of the present invention may be applied.
Figure 2:
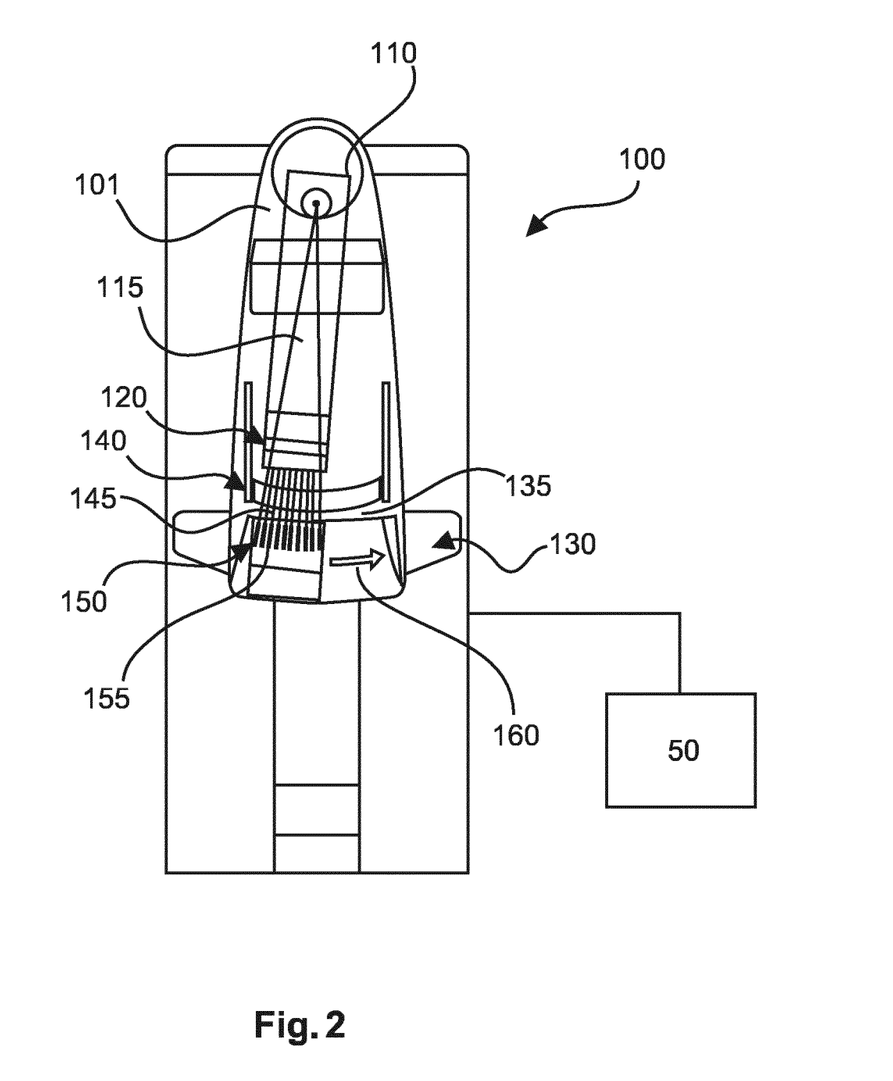

FIGS. 1 and 2 show a scanning mammography X-ray imaging device 100 to which principles of embodiments of the present invention may be applied. The scanning mammography X-ray imaging device 100 is a multi-slit X-ray scanner which is adapted for acquiring two-dimensional projection images for digital mammography. A patient is irradiated by a bundle of thin X-ray beams 145 each of which is detected by a corresponding line 155 of detector elements of an X-ray line detector 150. Each beam may have a rectangular cross-section being typically a few centimeters, for example 4 cm, wide and several tenth of micrometers, for example 50 μm, across. The narrow X-ray beams 145 are created by passing an initial X-ray beam 115 emitted by an X-ray source 110 through a collimator 120. This collimator 120 is a metal plate with several narrow linear apertures, also referred to as slits. For each slit there is one corresponding line 155 of detector elements in the X-ray line detector 150. Such line 155 may be a one-dimensional silicon array of pixel detectors for detector elements. The lines 155 are arranged to scan virtually a same area of the patient, yielding redundant information and enabling noise reduction. In FIG. 1, the line detectors 155 are mounted in an assembly of an X-ray line detector 150. A female breast to be irradiated may be compressed using a compression plate 140. The X-ray source 110 and the X-ray line detector 150 are coupled to a same arm 101 and are arranged at opposite sides with respect to an observation volume 135 between the compression plate 140 and the X-ray line detector 150. In the example shown in FIGS. 1 and 2, the arm 101 may be pivoted about a hinge situated close to the X-ray source 110 wherein a pivoting motion may be driven by a moving mechanism 130. The pivoting motion or scanning motion is indicated by the arrow 160 in FIG. 2 and is such that a center axis of the X-ray beam 115 is rotated around an axis orthogonal to this center axis.

In a scanning X-ray imaging device as or similar to the device 100 shown in FIGS. 1 and 2, features of embodiments of the present invention may be beneficial to reduce a patient X-ray dose and a local exposure time when the device is operated with a limited scan length, i.e. a limited motion distance along the direction 160. A modified scanning X-ray imaging device according to an embodiment of the present invention could be for example used in order to perform a stereo scan that may be needed for producing images related to biopsy targeting.

Particularly, in such scanning X-ray imaging device, a certain number of detector lines 155 may be required for building up a final image. The more lines 155 passing the object of interest, the more X-ray dose is delivered. Making use of many lines 155 of detector elements may have various advantages such as reducing a workload for the X-ray source 110, enabling to reduce random noise and producing a larger tomography angle (when the same device is also used for tomosynthesis) with other parameters kept constant as the more lines the wider is the detector arrangement.

However, a wider detector arrangement with many detector lines 155 may also have some disadvantages. In image areas where not the full detector arrangement has passed with all detector lines, i.e. in a start area and a stop area, there will be a dose profile. This may result in lower image quality with more noise in these areas. In particular if the scan length is short in relation to a detector arrangement width, this effect may be significant.

One example of such a case is when producing stereo images with the detector arrangement being tilted inside a patient support. In such scenario, the image should be as wide as possible but for geometrical reasons the scan length has to be kept to a minimum. Furthermore, X-ray dose exposure and local exposure time should be kept to a minimum.

In the following, differences in device structure as well as in operating principles between a conventional scanning X-ray imaging device and embodiments of a scanning X-ray imaging device according to the present invention will be described with respect to FIGS. 3 to 9. Therein, FIGS. 3 to 5 refer to a conventional device whereas FIGS. 6 to 9 refer to a device according to an embodiment of the present invention.

Figure 3:
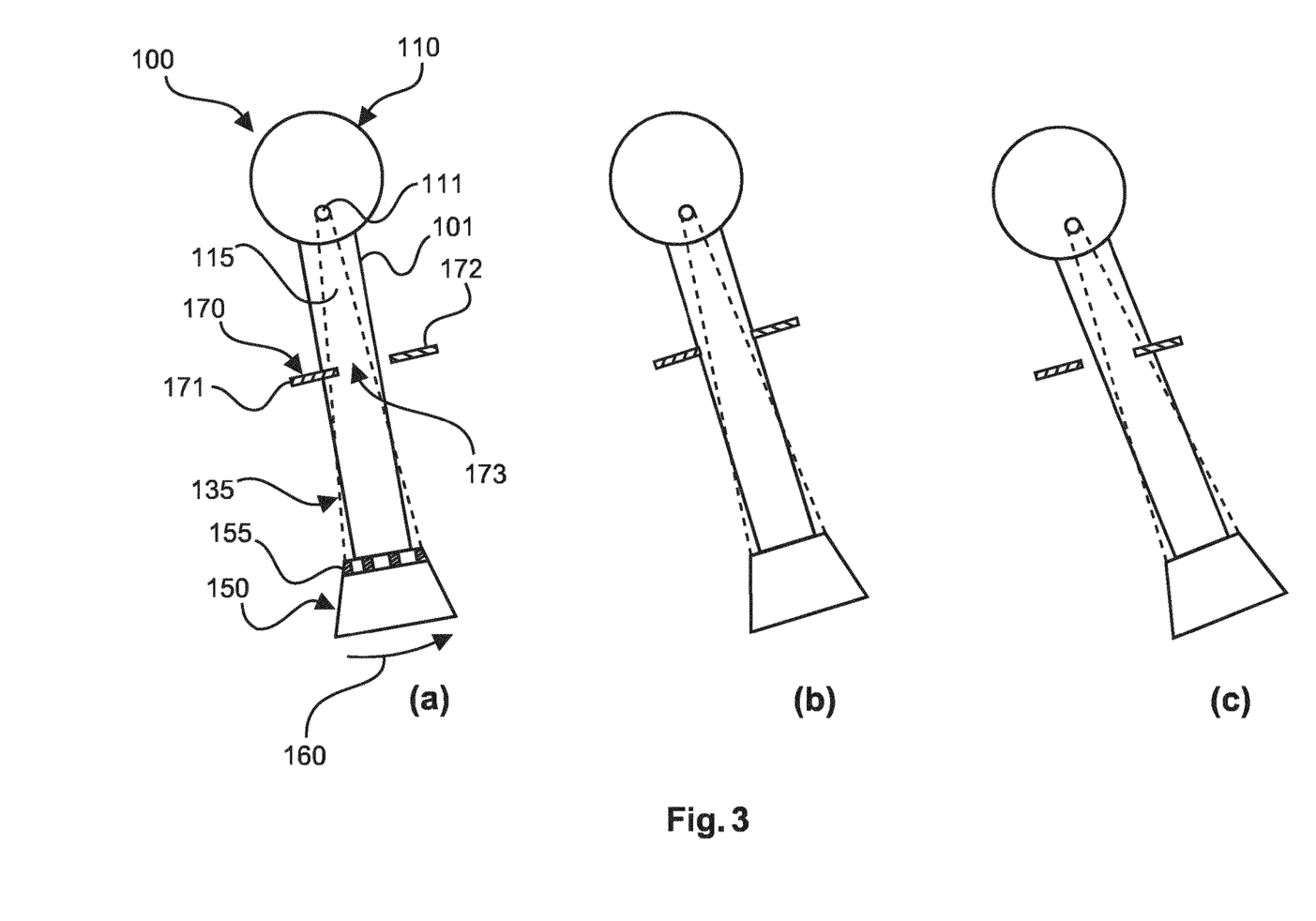
FIGS. 3(a)-(c) illustrate a scanning X-ray imaging device with a conventional field limiter arrangement comprising stationary shield plates at three stages of a scanning motion.
Figure 4:
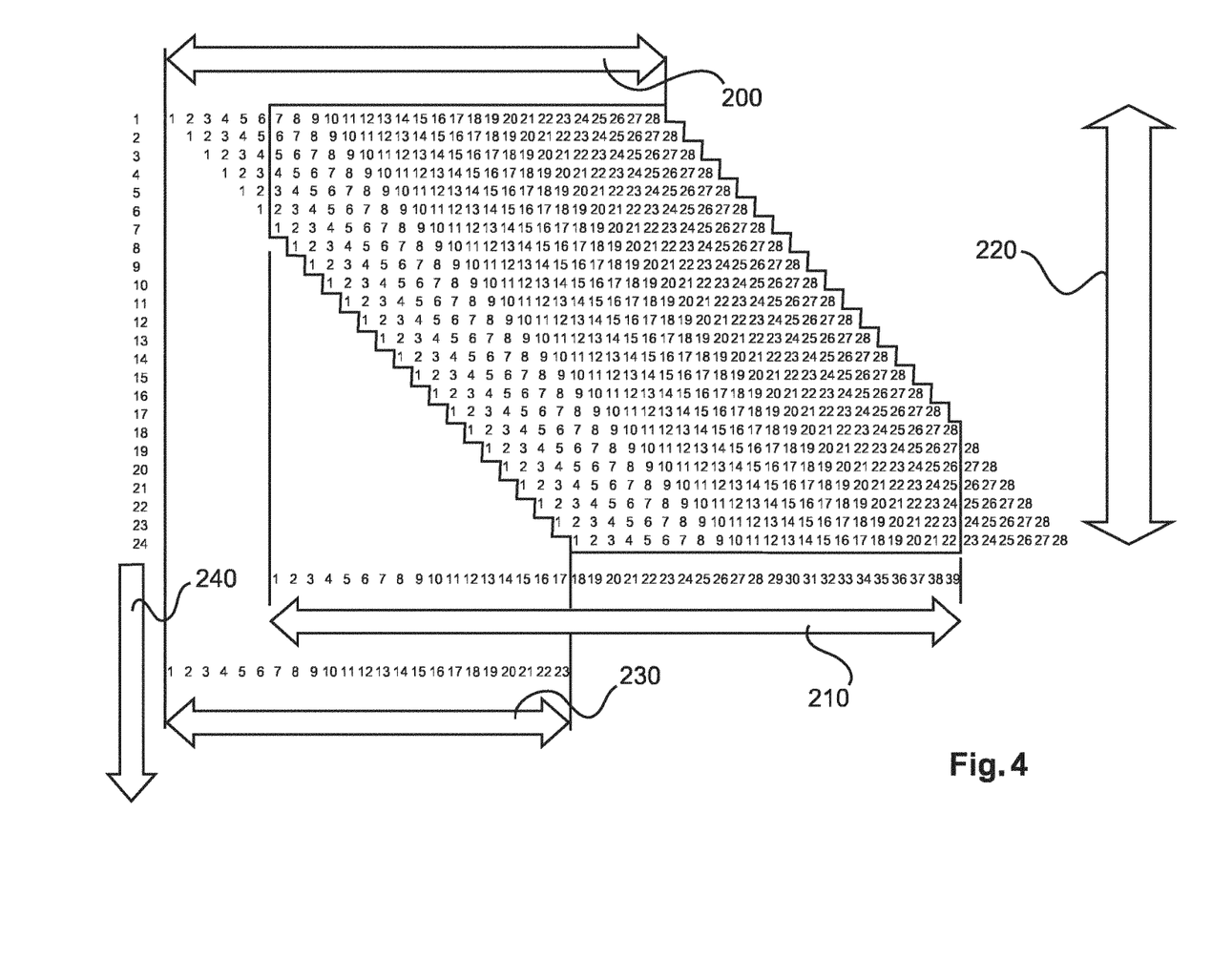
FIG. 4 illustrates operating principles of the device of FIG. 3.
Figure 5:
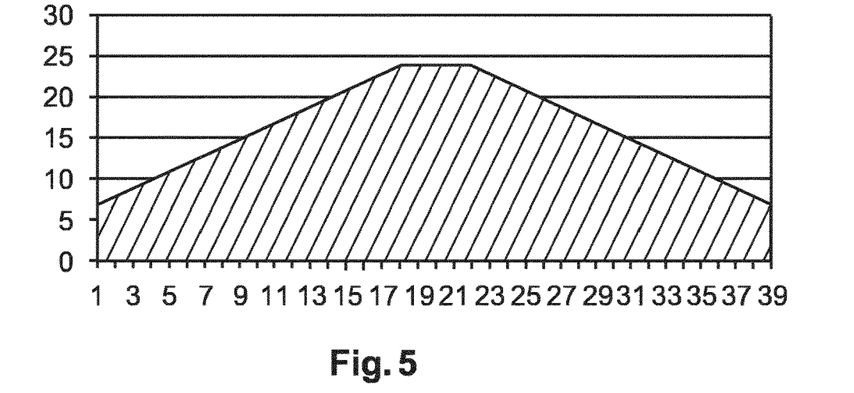
FIG. 5 illustrates a dose level distribution for the device of FIG. 3.
Figure 6:
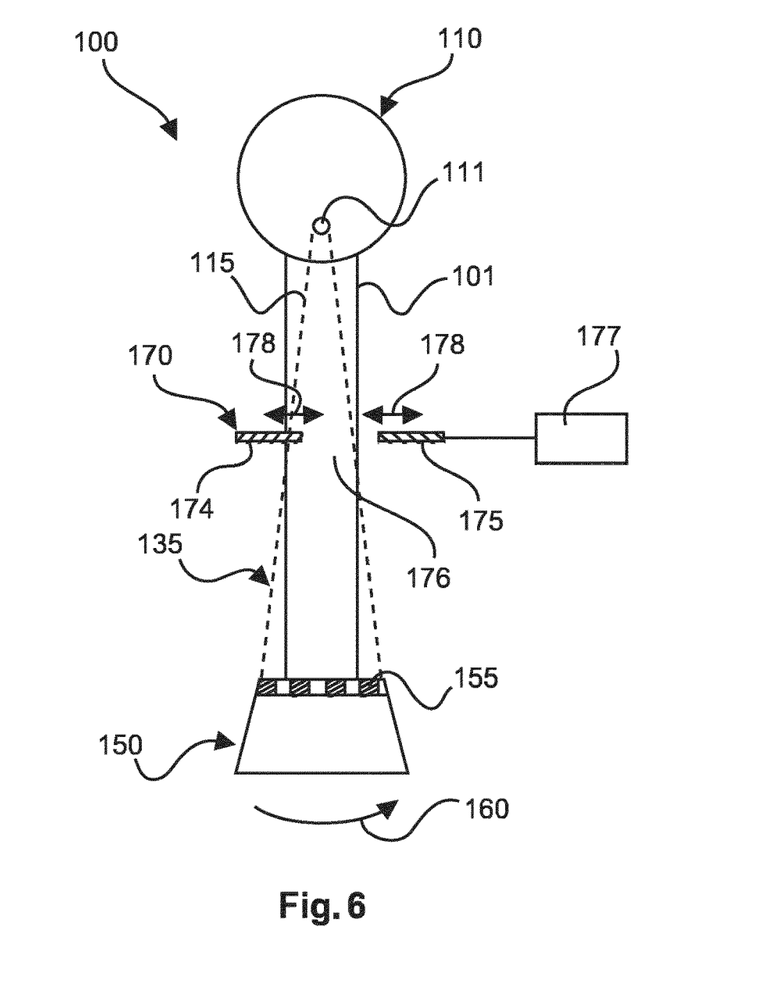
FIG. 6 schematically illustrates a scanning X-ray imaging device with a field limiter arrangement including two variable shield plates according to an embodiment of the present invention.
Figure 8:
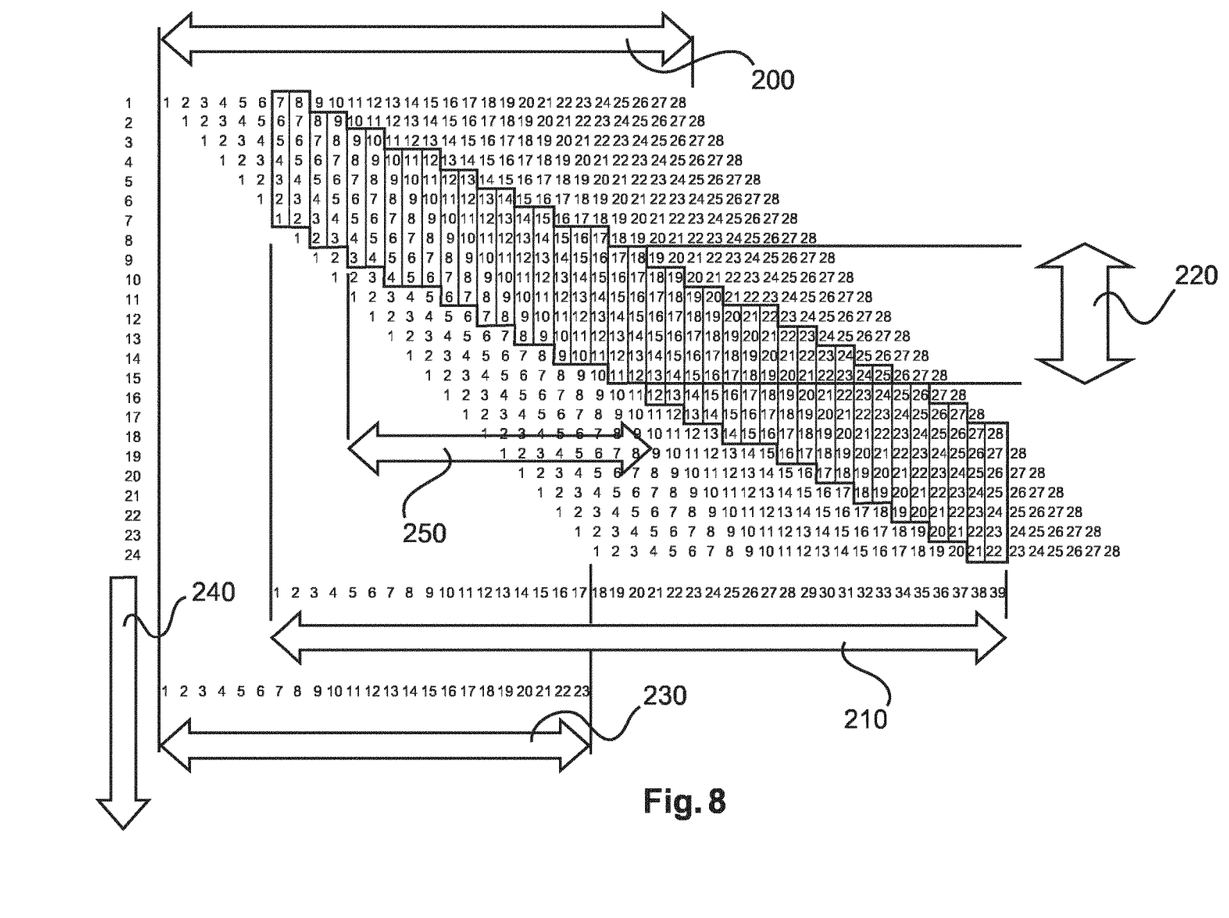
FIG. 8 illustrates operating principles of the device of FIG. 7.
Figure 9:
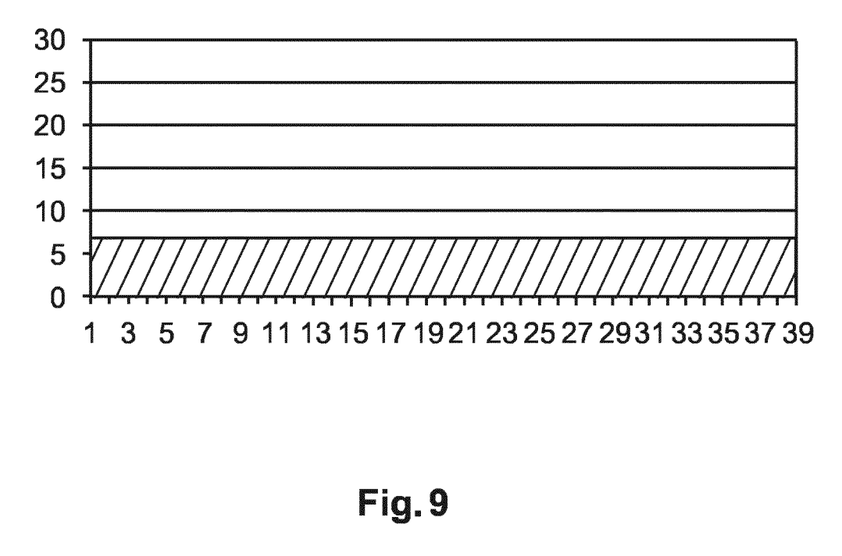
FIG. 9 illustrates a dose level distribution for the device of FIG. 7.

Particularly, FIG. 3 shows main features of a conventional scanning X-ray imaging device with a field limiter arrangement having fixed or stationary shield plates and the sequence of FIG. 3(a) to FIG. 3(c) illustrates an operating principle of such device. FIGS. 4 and 5 illustrate how lines of X-ray detector elements in an X-ray line detector of such conventional device are irradiated during normal operation, i.e. during an image acquisition procedure of short scan length, and a corresponding dose level distribution, respectively. FIG. 6 shows an embodiment of a scanning X-ray imaging device according to the present invention having a field limiter arrangement with two variable, i.e. displaceable, shield plates. The sequence of FIGS. 7(a)-(d) illustrates an operating principle of such device. FIGS. 8 and 9 illustrate irradiation characteristics of the lines of X-ray detector elements of an X-ray line detector of such inventive device and a corresponding dose level distribution, respectively.

Figure 7:
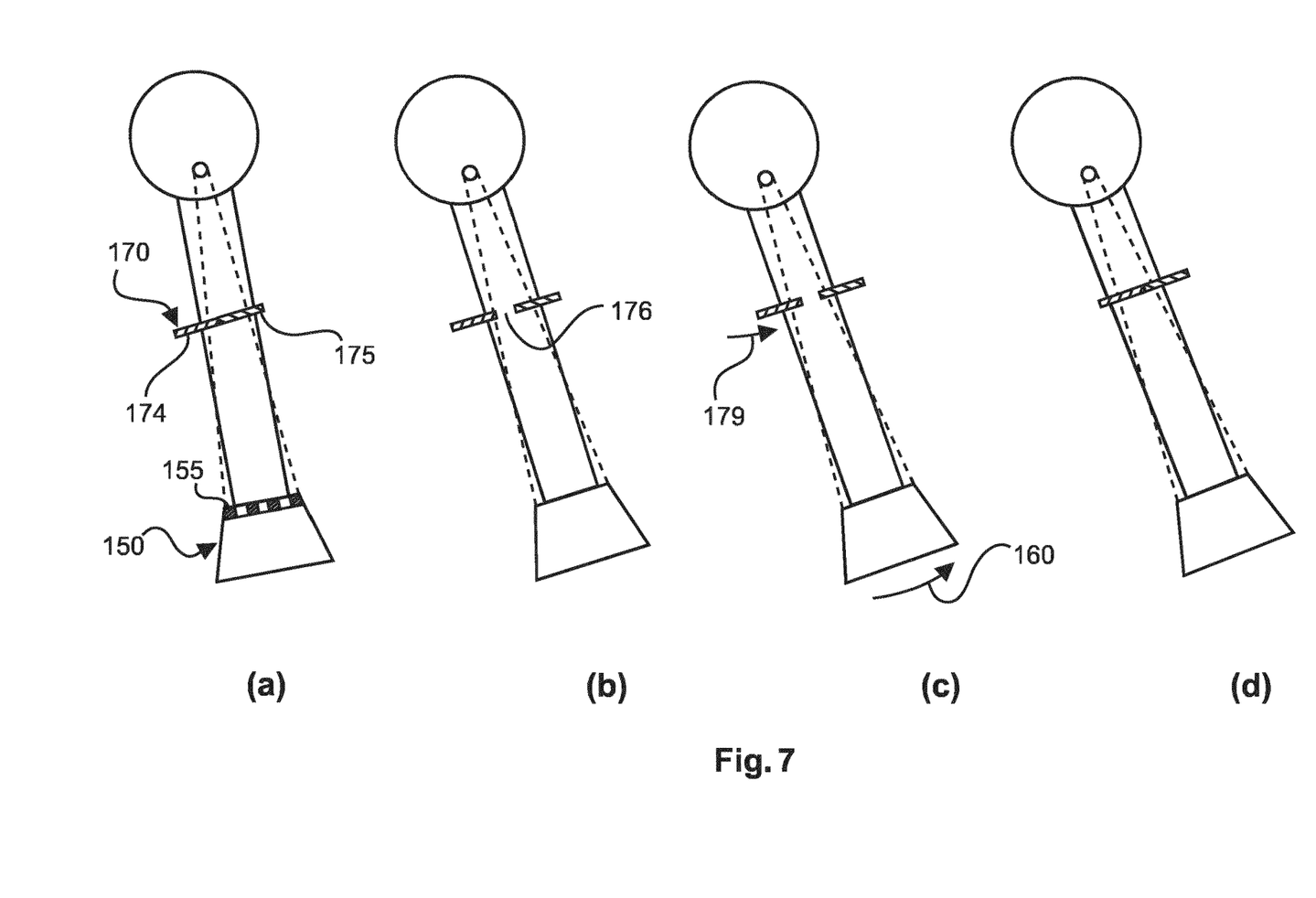
FIGS. 7(a)-(d) illustrate operating principles of the device of FIG. 6.

The conventional scanning X-ray imaging device 100 shown in FIG. 3 and the scanning X-ray imaging device according to an embodiment of the present invention shown in FIGS. 6 and 7 both comprise an X-ray source 110, an X-ray line detector 150, a field limiter arrangement 170 and an observation volume 135. The X-ray source 110 and the X-ray line detector 150 are mechanically coupled to each other via an arm 101. While FIGS. 3, 6 and 7 are only very schematical and only show these basic features of a scanning X-ray imaging device, one skilled in the art understands that such device 100 may comprise additional structural features and elements and the features and elements shown in the figures may be embodied in a more complex manner than shown in the figures.

The X-ray source 110 may be a conventional X-ray tube having a tube focus 111 from which an X-ray beam 115 is emitted towards the X-ray line detector 150.

The X-ray line detector 150 generally comprises multiple lines 155 of X-ray detector elements. Each line 155 comprises a plurality of X-ray detector elements arranged linearly in a line direction substantially orthogonal to the X-ray beam 115. In FIGS. 3 and 6, this line direction is orthogonal to the paper plane. Accordingly, when the X-ray line detector 150 is displaced along the scanning direction 160 by the moving mechanism 130, several of the lines 155 of X-ray detector elements are scanned through a region of interest of an object situated within the observation volume 135.

In the specific exemplary embodiment shown in the figures, the X-ray line detector 150 comprises four modules, each module comprising seven lines of X-ray detector elements such that the X-ray line detector 150 comprises a total of 28 lines 155 of X-ray detector elements (wherein in the figures, only four of these lines 155 are depicted). A width of the X-ray line detector 150 is about 67 mm. A scanning velocity along the scanning direction 160 will be tuned in such a way that a nominal image quality is reached after seven lines 155 of X-ray detector elements of scanning. Here, the nominal image quality typically refers to an image quality used in X-ray screening. An image width required is 93 mm in a plane of the X-ray line detector 150. Such image width may be relevant for biopsy applications. A scan movement will be 23 lines which corresponds to 55 mm with an X-ray line detector 150 as shown.

A scanning operation in this example may be a stereo scan. This means that two small two-dimensional scans are performed around a nominal angle of the scan arm 101 at +/−15°. Therein, a rotation axle is around the focus tube 111. An angle span of the scan arm 101 may be for example from 12.4°-17.6°.

The principle explained herein may be relevant for other dimensions as well as long as the scan length is short relative to the detector width.

A reason for the small scan length presented above may be that a detector movement is generally limited by a total height of a patient support table. In order to create a large enough image, i.e. in this case 93 mm at the detector plane, a scan velocity needs to be low so that contributions from few detector lines will be sufficient to reach the desired image quality, and the removed area with insufficient contributions is minimized. To maintain a feasible X-ray tube load and a desirable level of data redundancy and dose-uniformity at least one detector module, i.e. at least seven lines of X-ray detector elements, has to pass the object of interest. Accordingly, in order to gain image size in scan direction, the scan speed may be tuned down to give a nominal dose level (compared to a typical screening mammography dose) already after seven lines of X-ray detector elements. An object area passed by less than seven lines should preferably be shielded from X-ray dose since a resulting X-ray image will not reach a desired or required image quality. Making use of the method of slowing down the scan velocity to create an image already after seven lines of X-ray detector elements may be necessary to end up with a feasible relation between an image size and a total height of the patient support table.

However, in conventional devices as shown in FIG. 3, such method may result in significant problems. In such conventional devices 100, the field limiter arrangement 170 generally comprises fixed shield plates 171, 172 with an opening 173 of fixed cross-section between these shield plates. An area more central in the image will be generally scanned by more than the needed seven lines 155 of X-ray detector elements. This will generally build up both a dose level given to the tissue of a patient as well as a local exposure time of that tissue.

In the example shown, the X-ray line detector 150 comprises 28 lines of X-ray detector elements. If the scan length would be longer than the detector width, the central part of the object would receive approximately 4 times higher dose and exposure time than required for the nominal dose. The geometry of the example device 100 may however limit the dose somewhat since the scan length is shorter than the detector width. The required image width is about 93 mm at the detector plane and this requires a scan length of 55 mm. The detector width is assumed to be 67 mm. This means that the central part of the image will be scanned by a maximum of 24 lines 155 of X-ray detector elements, giving a factor for an extra (unnecessary) dose of 24/7=3.4 times. The same extra factor is also relevant for the local exposure time.

The sequence shown in FIGS. 3(a)-(c) illustrate an operating principle of the conventional scanning X-ray imaging device with fixed shielding plates 171, 172. FIG. 3(a) shows a start position in which seven lines are shielded by the left shield plate 171. FIG. 3(b) shows a middle position in which no lines 155 of X-ray detector elements are shielded by any of the shield plates 171, 172. FIG. 3(c) shows an end position in which seven lines 155 of X-ray detector elements are shielded by the right shield plate 172.

FIG. 4 illustrates the operation principle of the scanning X-ray imaging device 100 of FIG. 3 with an ordinary stationary field limiter arrangement 170 cutting off seven lines 155 of X-ray detector elements at a beginning and at an end of a scanning motion. The figure illustrates the X-ray line detector 150 with 28 lines 155 of X-ray detector elements moving from left to right, indicated by the arrow 200. The grey area represents the resulting image comprising in total 93 mm or 39 lines 155 of detector elements as indicated by the arrow 210. A sum of each grey column indicates a dose level and exposure time, starting and ending with a nominal dose created by seven lines 150 of X-ray detector elements as indicated by the arrow 220. The scan length is indicated by the arrow 230 and comprises 23 lines 155 of detector elements corresponding to 55 mm at the detector plane. The non-grey area in FIG. 4 indicates the detector lines 155 shielded by the standard stationary field limiter arrangement 170 since in such region the number of lines 155 for acquiring image information would be less than seven and thus the image quality would not be up to nominal level. The arrow 240 indicates the steps during a scanning motion.

FIG. 5 illustrates a dose level distribution when acquiring a scanning X-ray image as described above with reference to FIGS. 3 and 4. A number of lines 155 of X-ray detector elements irradiated during image acquisition corresponds to a dose level and is represented in FIG. 5 over the image width including 39 lines 155.

As evident from FIG. 5, the dose level and the local exposure time will vary over the image width. While at the start and stop positions, the nominal dose level corresponds to seven lines of X-ray detector elements, the dose level raises to 23 lines of X-ray detector elements at the middle of the image. Accordingly, in the conventional scanning X-ray imaging device with a fixed or stationary field limiter arrangement 170, there occurs excessive dose level or X-ray exposure at the middle of the image and an overall dose level is higher than required for acquiring a scanning X-ray image with sufficient image quality. FIG. 6 schematically illustrates a scanning X-ray imaging device 100 according to an embodiment of the present invention. Most of the components are same or similar to the components described above with respect to the conventional device 100 of FIG. 3 and therefore are indicated with the same reference signs.

However, the device 100 of FIG. 6 differs from conventional devices in that the field limiter arrangement 170 does not comprise stationary shield plates 171, 172 but comprises variable shield plates 174, 175 which may be displaced independently from each other. In other words, the variable shield plates 174, 175 may be displaces, inter alia, with respect to each other. Accordingly, a cross sectional area of an opening 176 between the variable shield plates 174, 175 may be varied by displacing the variable shield plates 174, 175. Furthermore, the variable shield plates 174, 175 may be specifically displaced such that a location of a centre of the opening 176 is displaced relative to the X-ray line detector 150.

A displacing mechanism 177 is provided for displacing each of the variable shield plates 174, 175. Therein, the displacement mechanism 177 may displace the variable shield plates 174, 175 in a plane parallel to a detection surface of the X-ray line detector 150 and in a direction 178 orthogonal to a line direction in which the lines 155 of X-ray detector elements are oriented.

FIGS. 7(a) to 7(d) show a sequence of operation steps performed during a scanning motion of an image acquisition procedure using the inventive scanning X-ray imaging device of FIG. 6.

In a first step as shown in FIG. 7(a), the field limiter arrangement 170 is controlled such that all lines 155 of detector elements of the X-ray line detector 150 are shielded, i.e. the field limiter arrangement 170 is completely closed. The left shield plate 174 shields seven lines 155 of detector elements and is steady in room. The right plate 175 is arranged directly adjacent to the left plate 174. A detector scan starts at a relative speed 1. The right shield plate 175 starts displacing with a relative speed about 16/7, i.e. about 2 times faster than the speed of the detector.

In a second step as shown in FIG. 7(b), in which the detector 150 has moved by 7 steps, i.e. by 7 lines 155 of detector elements, the left shield plate 174 does not shield any lines 155 of detector elements anymore. The opening 176 or gap between the shield plates 174, 175 has opened to 16 lines 155 of detector elements with a linear motion, i.e.

at constant speed. At such stage, the left shield plate 174 starts moving with the same speed as the right shield plate 175, i.e. at a relative speed of 16/7.

In a third step as shown in FIG. 7(*c*), in which the detector 150 has moved by 18 lines 155 of detector elements, the opening 176 is still opened to 16 lines 155 of detector elements. At this stage, the left shield plate 174 shields 13 lines 155 of detector elements, the right shield plate 175 shields no lines 155 of detector elements. Here, the right shield plate 175 is stopped moving and is kept steady in room. The left shield plate 174 continues to move with the same speed, i.e. a relative speed of 16/7.

In a fourth step as shown in FIG. 7(*d*), in which the detector 150 has moved by 23 lines 155 of detector elements, the opening 176 is again closed completely and all lines 155 of detector elements are shielded. The detector scan, i.e. the image acquisition procedure, may stop at this stage. The width of the produced image is 39 lines, i.e. about 93 mm in the detector plane.

Overall, during the image acquisition procedure illustrated in FIGS. 7(*a*)-(*d*), the moving mechanism 130 is controlled to perform a scanning motion such that at least portions of the X-ray beam are scanned in a direction 160 through a region of interest within the observation volume and, synchronously herewith, the displacing mechanism 177 is controlled such that the opening 176 between the variable shield plates 174, 175 is first successively opened to a larger cross section, then kept at a constant cross section for a while and then finally closed again to a smaller cross section successively. During the displacing motion of the shield plates 174, 175, the opening 176 there between is continuously moved relative to the X-ray line detector 150, i.e. in the direction 179 shown in FIG. 7(*c*).

Accordingly, at the beginning of the image acquisition procedure (stages in and shortly after the stage shown in FIG. 7(*a*)), the shield plates 174, 175 are only slightly opened and the opening 176 is closer to a left edge of the X-ray detector 150. Then, in the middle of the image acquisition procedure (stages between the stages shown in FIG. 7(*b*) and FIG. 7(*c*)), the shield plates 174, 175 are opened to a maximum and the opening 176 is situated somewhere between the left and right edges of the X-ray detector 150. At the end of the image acquisition procedure (stages in and shortly before the stage shown in FIG. 7(*d*)), the shield plates 174, 175 are again only slightly opened and the opening 176 is closer to a right edge of the X-ray detector 150.

FIG. 8 illustrates the operation principle of the inventive scanning X-ray imaging device 100 of FIGS. 6 and 7 with a field limiter arrangement 170 including variable shield plates 174, 175. Similar to FIG. 4, FIG. 8 illustrates the X-ray line detector 150 with 28 lines 155 of X-ray detector elements moving from left to right, indicated by the arrow 200. The grey area represents the resulting image comprising in total 93 mm or 39 lines 155 of detector elements as indicated by the arrow 210. A sum of each grey column indicates a dose level.

In contrast to the conventional case shown in FIG. 4, the device according to embodiments of the present invention allows to keep constant the dose level and exposure time for all sub-regions of the scanned region of interest as indicated by the arrow 220. This means that also the image quality will be uniform. In the presented example, the dose level and exposure time constantly corresponding to 7 lines 155 of detector elements, as also shown in FIG. 9. The scan length is indicated by the arrow 230 and comprises 23 lines 155 of detector elements corresponding to 55 mm at the detector plane. The non-grey area in FIG. 8 indicates the detector lines 155 shielded by the field limiter arrangement 170 since in such region the number of lines 155 for acquiring image information would be less than seven and thus the image quality would not be up to nominal level. The arrow 240 indicates the steps during a scanning motion. The arrow 250 indicates the maximum opening 176, i.e. the maximum field limiter width, of 16 lines 155 of detector elements, corresponding to 38 mm.

FIG. 9 illustrates a dose level distribution when acquiring a scanning X-ray image as described above with reference to FIGS. 7 and 8. A number of lines 155 of X-ray detector elements irradiated during image acquisition corresponds to a dose level and is represented in FIG. 5 over the image width including 39 lines 155. This number of lines 155 of X-ray detector elements is constant throughout the entire image width. Accordingly, in the inventive scanning X-ray imaging device with a variable field limiter arrangement 170, there occurs no excessive dose level or X-ray exposure at the middle of the image and an overall dose level is permanently kept at a required minimum for sufficient image quality.

Summarizing, a scanning X-ray imaging device 100 is proposed. The device may be specifically adapted for mammography applications. The device comprises an X-ray source 110, an X-ray line detector 150, a field limiter arrangement 170 and an observation volume 135. The field limiter arrangement 170 comprises at least two variable shield plates 174, 175 enclosing an opening 176 and a displacing mechanism 177. The shield plates may be displaced with respect to a center axis of an X-ray beam 115 by means of the displacing mechanism such as to vary at least one of a cross-section and a location of the opening 176 between the shield plates 174, 175 through which at least a part of the X-ray beam 115 is transmitted. The shield plates may be displaced independently from each other by means of the displacing mechanism 177. Such device 100 may be operated to perform a scanning motion such as to scan at least portions of the X-ray beam through a region of interest within the observation volume 135 and, at the same time, control the displacing mechanism 177 such that the opening 176 between the shield plates 174, 175 is first successively opened to a larger cross-section and then successively closed again to a smaller cross-section during the scanning motion. Thereby, an X-ray dose level and an X-ray exposure time may be kept constant throughout an image acquisition procedure and an overall dose level may be minimized.

LIST OF REFERENCE SIGNS 100 scanning X-ray imaging device
101 arm
110 X-ray source
115 X-ray beam
120 collimator
130 moving mechanism
135 observation volume
140 compression plate
145 bundle of thin X-ray beams
150 X-ray line detector
155 line of X-ray detector elements
160 scanning direction
170 field limiter arrangement
171 stationary shield plate
172 stationary shield plate
173 opening
174 left variable shield plate 175 right variable shield plate
176 opening
177 displacing mechanism
178 displacing direction
200 detector width
210 image width
220 local dose and exposure time
230 scan length
240 motion steps in scanning dire
250 field limiter width

The invention claimed is:

1. A scanning X-ray imaging device comprising:
an X-ray source;
an X-ray line detector including a first edge and a second edge that are disposed on opposite sides of the X-ray line detector;
a field limiter arrangement; and
an observation volume;
wherein the X-ray source is adapted to emit an X-ray beam towards the X-ray line detector;
a moving mechanism coupled to at least one of the X-ray source and the X-ray line detector, the moving mechanism adapted to perform a scanning motion such as to scan at least portions of the X-ray beam through a region of interest within the observation volume;
wherein the observation volume is arranged between the X-ray source and the X-ray line detector;
wherein the field limiter arrangement is arranged between the X-ray source and the observation volume;
wherein the field limiter arrangement comprises at least two variable shield plates and a displacing mechanism;
wherein the shield plates may be displaced with respect to the center axis of the x-ray beam by the displacing mechanism such as to vary a cross section of an opening between the shield plates through which at least a part of the X-ray beam is transmitted; and
wherein the shield plates may be displaced independently from each other by the displacing mechanism; and
wherein the independent displacing of the shield plates is controlled by the displacing mechanism such that, as a center of the opening between the shield plates moves from the first edge side of the X-ray line detector to the second edge side of the X-ray line detector, the opening between the shield plates is successively opened to a larger cross section and then closed to a smaller cross section during the scanning motion.

2. The X-ray imaging device of claim 1, wherein the X-ray line detector comprises multiple lines of X-ray detector elements arranged in a line direction orthogonal to the X-ray beam and wherein the displacement mechanism is adapted to displace each of the shield plates in a direction orthogonal to the line direction.

3. The X-ray imaging device of claim 2, wherein the X-ray line detector comprises more lines of X-ray detector elements than seven lines of X-ray detector elements.

4. The X-ray imaging device of claim 1, wherein the X-ray source and the X-ray line detector are coupled to the moving mechanism such that a center axis of the X-ray beam may be rotated around an axis orthogonal to the center axis.

5. The X-ray imaging device of claim 4, wherein the moving mechanism is adapted to move the X-ray beam such as to displace the center axis of the X-ray beam within the observation volume in order to thereby scan the X-ray beam through a region of interest within the observation volume.

6. The X-ray imaging device of claim 5, wherein each of the shield plates is adapted to substantially absorb X-rays.

7. The X-ray imaging device of claim 1, wherein the X-ray imaging device is a scanning mammography X-ray imaging device.

8. A method for operating an X-ray imaging device, the method comprising:
controlling a moving mechanism to perform a scanning motion to scan at least portions of an X-ray beam through a region of interest within an observation volume; and
controlling a displacing mechanism to achieve a uniform dose level distribution such that, as a center of an opening between shield plates moves from a first edge side of an X-ray line detector to a second edge side of the X-ray line detector, the opening between the shield plates is successively opened to a larger cross section and then closed to a smaller cross section during the scanning motion, the first edge of the X-ray detector and the second edge of the X-ray detector being disposed on opposite sides of the X-ray line detector.

9. The method of claim 8, wherein the displacing mechanism is controlled such that, during the scanning motion, the center the opening between the shield plates moves relative to an X-ray line detector.

10. The method of claim 8, wherein at a beginning of an image acquisition procedure during the scanning motion, the displacing mechanism is controlled such that a smaller number of lines of X-ray detector elements closer to the first edge of the X-ray detector is irradiated through the opening between the shield plates than the number of irradiated lines away from the first edge and at an end of an image acquisition procedure during the scanning motion, the displacing mechanism is controlled such that a smaller number of lines of X-ray detector elements closer to the second edge of the X-ray detector opposite to the first edge is irradiated through the opening between the shield plates than the number of irradiated lines away from the second edge.

11. The method of claim 8, wherein a displacement velocity of the opening between the shield plates in a lateral direction is high enough such that the portion of the X-ray beam transmitted through this opening is displaced laterally with such velocity that, at a location of a surface of an X-ray detector, the X-ray beam moves faster than the motion of the X-ray detector itself.

12. A non-transitory computer-readable medium storing computer-readable instructions, which, when executed by a processor, cause the processor to perform a method comprising:
controlling a moving mechanism to perform a scanning motion such as to scan at least portions of an X-ray beam through a region of interest within an observation volume; and
controlling a displacing mechanism to achieve a uniform dose level distribution such that, as a center of an opening between shield plates moves from a first edge side of an X-ray line detector to a second edge side of the X-ray line detector, the opening between the shield plates is successively opened to a larger cross section and then closed to a smaller cross section during the scanning motion, the first edge of the X-ray detector and the second edge of the X-ray detector being disposed on opposite sides of the X-ray line detector.

* * * * *